Figure 1:
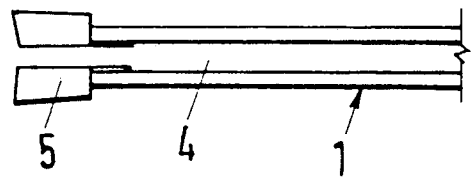
Figure 1:
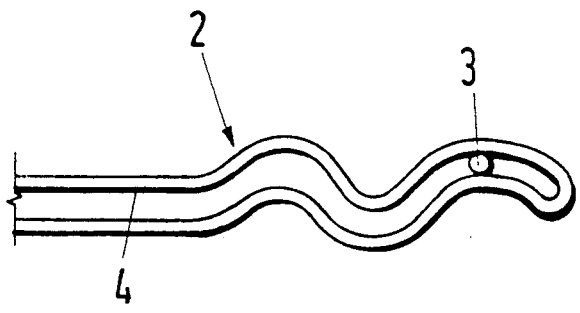

United States Patent [19]

Rossdeutscher

[11] Patent Number: 5,047,013
[45] Date of Patent: Sep. 10, 1991

[54] VARICOSE VEIN PROBE WITH HOLLOW CURVED SPIRAL TIP

[75] Inventor: Sonja Rossdeutscher, Dortmund, Fed. Rep. of Germany

[73] Assignee: Astra Meditec AB, Molndal, Fed. Rep. of Germany

[21] Appl. No.: 404,589

[22] Filed: Sep. 8, 1989

[30] Foreign Application Priority Data

Sep. 10, 1988 [DE] Fed. Rep. of Germany ....... 3830909

[51] Int. Cl.$^5$ .............................................. A61M 25/00
[52] U.S. Cl. .................................. 604/53; 604/264; 604/272; 604/282
[58] Field of Search ...................... 604/51, 48, 93, 264, 604/272, 274, 281, 282, 902, 52, 53

[56] References Cited

U.S. PATENT DOCUMENTS

| | | | |
|---|---|---|---|
| 1,273,665 | 7/1918 | Porter | 604/264 |
| 1,626,839 | 5/1927 | Kallmeyer | 604/264 |
| 2,268,321 | 12/1941 | Flynn | 604/273 X |
| 3,618,614 | 11/1971 | Flynn | 604/282 |
| 3,741,214 | 6/1973 | Tillander | 606/159 |
| 4,236,520 | 12/1980 | Anderson | 604/264 |
| 4,323,072 | 4/1982 | Rosenbluth et al. | 604/275 |
| 4,345,602 | 8/1982 | Yoshimura et al. | 604/275 X |
| 4,643,716 | 2/1987 | Drach | 604/281 X |
| 4,787,889 | 11/1988 | Steppe et al. | 604/22 |
| 4,790,830 | 12/1988 | Hamacher | 604/274 |

FOREIGN PATENT DOCUMENTS

| | | |
|---|---|---|
| 0014424 | 3/1983 | European Pat. Off. . |
| 2062204 | 8/1971 | Fed. Rep. of Germany . |
| 7337742 | 2/1974 | Fed. Rep. of Germany . |
| 1409284 | 7/1988 | U.S.S.R. .............................. 604/93 |

Primary Examiner—C. Fred Rosenbaum
Assistant Examiner—Adam J. Cermak
Attorney, Agent, or Firm—Michael L. Dunn

[57] ABSTRACT

The invention relates to a probe for treating varicose veins, comprising a flexible plastic tube with a tip portion which can be guided through varicose veins at its front end, the tube being at least as long as the veins to be treated. To enable a sclerosing agent to be injected at desired points along the varicose vein, the invention proposes that the probe should have at least one lateral opening in the region of the tip portion, and that the inner cavity of the tube should form a flow connection from a joining piece at the rear end of the tube to the lateral opening, for injection of sclerosing agent.

8 Claims, 1 Drawing Sheet ated.
VARICOSE VEIN PROBE WITH HOLLOW CURVED SPIRAL TIP The invention relates to a probe for treating varicose veins. It comprises a flexible plastic tube with a tip portion which can be guided through varicose veins at its front end, the tube being at least as long as the vein to be treated. A probe of this type is known, for example, from De-PS 20 62 204. The probes described in this specification and other known ones are generally used to strip affected veins. For this purpose the tip of the probe is inserted at one end of the vein to be removed, and the probe is guided through the whole length of the vein and brought out through a surgical incision at the other end. The end of the probe becomes hooked onto the vein at the insertion opening, so the whole vein is drawn out by pulling the tip portion. This surgical operation is generally carried out under complete narcosis.

Some of the known vein probes are also tubular, but instead of the internal tube cavity being open to carry liquids it is generally filled by a wire. The wire dictates the flexibility or rigidity of the probe but also serves to take up the tensile forces when the vein is pulled out.

Although other probes which can be inserted in veins or arteries are known under the designation of catheters, these either comprise a very soft, flexible plastic tube which is more or less floated into the vein or artery with the blood stream, or they have a guide wire and a more or less sharp edged tip which can only be inserted in the blood vessel under radiological control.

It is virtually impossible to insert the first mentioned type of catheter in varicose veins, as the blood stream has more or less come to a standstill in them. It is very expensive to insert the second type under radiological control, and the doctor and patient are also exposed to a certain amount of radiation. In addition it is difficult to insert conventional catheters in varicose veins, because the incorrectly functioning vein valves and other pathological changes set up resistance to the catheter, and there is an inevitable risk of injury or of the vein wall being punctured. On the other hand the known varicose vein probes on which the invention is based can be inserted in veins without much trouble by a skilled surgeon.

However these conventional probes have the drawback that they can virtually only be used to pull out veins, and other methods of treatment cannot be applied. The problem underlying the invention is therefore to provide a probe with which inter alia varicose veins can be atrophied (sclerosed).

The problem is solved in that the probe has at least one lateral opening in the region of the tip portion, and that the inner cavity of the tube forms a flow connection from a joining piece at the rear end of the tube to the opening in the tip portion, for injection of a sclerosing agent.

In contrast with the conventional vein probes the cavity in the plastic tube is not completely filled by a wire. Hence a liquid can be injected through the probe into the vein, provided that the tube contains a suitable opening. However, the opening should not be in the tip of the tube (a) as the tip should be rounded to improve insertion and (b) because the sclerosing agent cannot be discharged accurately enough through the existing end of the tube. The lateral opening according to the invention enables the sclerosing agent to be ejected at the exact points where it is required. These are in particular the connections with the rest of the vein system.

It has been found advantageous to have the lateral opening in the front third of the tip portion. The veins to be treated may be really long, and the sclerosing agent must sometimes be injected at points very far removed from the insertion opening. Hence the lateral opening should advantageously be as far forward as possible, i.e. within the front third of the tip portion. However it may, if desired, be further back, at or in front of the rear end of the tip portion. The tip portion area may also contain a plurality of lateral openings.

It has further been found advantageous for the tip portion to be curved in a spiral. An embodiment of this type facilitates insertion of the probe in the pathologically affected veins.

It may finally be desirable for the plastic tube to have a wire reinforcement as well as the flow connection between the joining piece and the hole in the tip. The reinforcement may be provided eccentrically relative to the cross section of the tube and may serve inter alia to provide the desired rigidity or flexibility. Alternatively the wire may be provided at the centre of the cross section of the tube, if the flow connection is eccentric or if the internal cavity has a large enough cross section to provide a flow connection as well as containing the wire.

The joining piece at the rear end of the tube may be one conventionally used for syringes. Alternatively, the cross section of the tube may be shaped so that a syringe or other supply means for the sclerosing agent can be attached directly to the rear end of the tube. In this case the joining piece is so to speak formed by the severed end of the tube.

Other advantages and features of the invention will become clear from the following description of a preferred embodiment and from the accompanying drawing in which:

FIG. 1 shows the design of a varicose vein probe diagrammatically.

Referring to FIG. 1, this shows the design of the new probe in a fragmentary way and in longitudinal section. It substantially comprises a plastic tube 1 with an internal cavity 4 and a tip portion 2. The tip portion 2 is wound in a spiral and rounded at its front end. A the rear end there is a joining piece 5 for a syringe. The piece 5 may e.g. be fitted with a valve or a membrane which can be pierced. Alternatively the tube may have a cross section such that the rear end itself forms the joining piece. In particular, the probe may be mass produced at a maximum length and shortened by the required amount when used, with the rear end that is left forming the joining piece. Irrespective of this the joining piece provided could be detachable from the tube and replaced when the tube has been shortened.

The lateral opening 3 is in the front third of the tip portion 2. The spiral winding and the rounding of the front end of the tip portion 2 enable the probe to be inserted in the vein virtually without any problems. The tube is preferably made of a plastic material which can bend resiliently and yet has adequate rigidity.

The reason for providing the opening 3 at the side of the tip portion 2 is to enable the sclerosing agent to be injected directly into areas where there are connections with the rest of the vein system. The new probe can sclerose varicose veins over their whole length, by injecting the sclerosing agent through the side opening, over the whole length of the vein, while the probe is being inserted in or withdrawn from the vein.

Sclerosing agents or vein atrophying agents which can be injected through the side opening have been known for a long time. One such agent is Varigloban ®.

Operative removal of varicose veins by pulling them out with the known probes can be avoided, since the new probe enables the vein and particularly the areas connecting it to the adjacent vein system to be atrophied. This has considerable advantages for the patient. If the new probe and the sclerosing process described are used local anaesthesia is sufficient and complete narcosis is not required.

Furthermore the treatment can be given on an out-patient basis, whereas the conventional stripping of varicose veins requires in-patient treatment. The pulling of the veins is also far more traumatic and there is more haematoma than if the new probe is used.

On some occasions the pulling out of the veins leads to post-operative sensitivity disorders, but there is no danger of this if the new probe is used and the treatment restricted to sclerosing.

Finally, after treatment with the new probe and application of a suitable dressing the patient can walk unrestricted, whereas after treatment by the conventional process with known probes the leg can only gradually start bearing a weight again.

I claim:

1. A probe for treating varicose veins, comprising a flexible plastic tube having a circular cross section with a tip portion at least a part of which is curbed in a spiral and having a closed rounded front end thereon, which can be guided through varicose veins at its front end, and wherein the circular cross-section is within at least a portion of said spiral, the tube being at least as long as the vein to be treated, wherein said probe has at least one lateral opening in the spiral of said tip portion and removed from said front end, and an inner cavity of said tube forming a flow connection from a joining piece at a rear end of said tube to said lateral opening in said tip portion for injection of a sclerosing agent.

2. The probe as recited in claim 1 wherein said lateral opening is in the front third of said tip portion.

3. The probe of claim 2 wherein said tip portion is curved in a spiral.

4. The probe of claim 3 wherein said plastic tube has a reinforcement.

5. The probe of claim 2 wherein said plastic tube has a reinforcement.

6. The probe of claim 1 wherein said plastic tube has a reinforcement.

7. The probe of claim 1 wherein said plastic tube has a reinforcement.

8. A method for treating varicose veins which comprises: inserting a probe into the vein and injecting a sclerotizing agent through a lateral opening in the probe into the vein, proximate the location of branches from the vein, said probe comprising a flexible plastic cylindrical tube with a tip portion, having a closed rounded end thereon, which can be guided through varicose veins at its front end, the tube being at least as long as the vein to be treated, wherein said probe has at least one lateral opening in the region of the tip portion, an inner cavity of said tube forming a flow connection from a joining piece at a rear end of said tube to the lateral opening in the tip portion for injection of the sclerosing agent.

* * * * *